US005627267A

United States Patent [19]
Lyman et al.

[11] Patent Number: 5,627,267
[45] Date of Patent: May 6, 1997

[54] CYTOKINE DESIGNATED ELK LIGAND

[75] Inventors: Stewart Lyman, Seattle; M. Patricia Beckmann, Poulsbo; Peter R. Baum, Seattle, all of Wash.

[73] Assignee: Immunex Corporation, Seattle, Wash.

[21] Appl. No.: 458,077

[22] Filed: Jun. 1, 1995

Related U.S. Application Data

[60] Division of Ser. No. 213,403, Mar. 15, 1994, Pat. No. 5,512,457, which is a continuation-in-part of Ser. No. 977,693, Nov. 13, 1992, abandoned.

[51] Int. Cl.$^6$ .................................................. C07K 14/52
[52] U.S. Cl. .................... 530/351; 424/85.1; 435/69.5; 536/23.5; 935/9; 930/140
[58] Field of Search ................... 530/351; 424/85.1; 514/12; 435/69.5; 536/23.5; 935/9; 930/140

[56] References Cited

U.S. PATENT DOCUMENTS

| | | | |
|---|---|---|---|
| 5,134,121 | 7/1992 | Mobley et al. | 514/14 |
| 5,512,457 | 4/1996 | Lyman et al. | 435/69.5 |
| 5,516,658 | 5/1996 | Beckmann et al. | 435/69.5 |

FOREIGN PATENT DOCUMENTS

| | | |
|---|---|---|
| 0455093A2 | 11/1991 | European Pat. Off. . |
| 0597503A2 | 5/1994 | European Pat. Off. . |
| WO91/03569 | 3/1991 | WIPO . |
| WO92/18112 | 10/1992 | WIPO . |
| WO93/00425 | 1/1993 | WIPO . |

OTHER PUBLICATIONS

Cerretti et al., "Isolation of cDNAs that Encode Ligands to the Receptor Tyrosine Kinases Hek and Elk: Emergence of a Family of Proteins that are Ligands for the Eph Related Kinases (LERKS)", Abstract for American Assoc. for Cancer Research conference on Growth Factors, Development, and Cancer, held in Interlaken, Switzerland, Mar. 5–11, 1994.
Lyman et al., "Identification of a Ligand for the Elk Tyrosine Kinase Receptor", *Lymphokine and Cytokine Research*, vol. 12, No. 5, Abstract No. 92, Oct., 1993.
Beckmann et al., "Molecular Characterization of a Family of Ligands for Eph–Related Tyrosine Kinases, Abstract for Keystone Symposium on Inflammation, Growth Regulatory Molecules, and Atherosclerosis", Keystone, CO, Jan. 16–23, 1994.
M. Flint Beal, "Role of excitotoxicity in human neurological disease", *Current Opinion in Neurobiology,* 2:657–662, 1992.
Dennis W. Choi, "Excitotoxic Cell Death", *J. Neurobiology,* 23:1261–1276, 1992.
Massieu et al., "A Comparative Analysis of the Neuroprotective Properties of Competitive and Uncompetitive N–Methyl–D–Aspartate Receptor Antagonists In Vivo: Implications for the Process of Excitotoxic Degeneration and its Therapy", *Neuroscience,* 55:883–892, 1993.
Albin and Greenamyre, "Alternative excitotoxic hypotheses", *Neurology* 42:733–738, 1992.
Letwin et al., "Novel protein–tyrosine kinase cDNAs related to fps/fes and eph cloned using anti–phosphotyrosine antibody", *Oncogene* 3:621–627, 1988.
Lhotak et al., "Characterization of Elk, a Brain–Specific Receptor Tyrosine Kinase", *Mol. Cell. Biol.* 11:2496–2502, 1991.
Boyd et al., "Isolation and Characterization of a Novel Receptor–type Protein Tyrosine Kinase (hek) from a Human Pre–B Cell Line", *J. Biol. Chem.* 267:3262–3267, 1992.
Wicks et al., "Molecular cloning of HEK, the gene encoding a receptor tyrosine kinase expressed by human lymphoid tumor cell line", *Proc. Natl. Acad. Sci. USA* 89:1611–1615, 1992.
Sajjadi et al., "Identification of a New eph–Related Receptor Tyrosine Kinase Gene From Mouse and Chicken That Is Developmentally Regulated and Encodes at Least Two Forms of the Receptor", *New Biol.* 3:769–788, 1991.
Chan and Watt, "eek and erk, new members of the eph subclass of receptor protein–tyrosine kinases", *Oncogene* 6:1057–1061, 1991.
Lindberg et al., "cDNA Cloning and Characterization of eck, an Epithelial Cell Receptor Protein–Tyrosine Kinase in the eph/elk Family of Protein Kinases", *Mol. Cell. Biol.* 10:6316–6324, 1990.
Pasquale, "Identification of chicken embryo kinase 5, a developmentally regulated receptor–type tyrosine kinase of the Eph family", *Cell Regulation* 2:523–534, 1991.
Hirai et al., "A Novel Putative Tyrosine Kinase Receptor Encoded by the eph Gene", *Science* 238:1717–1720, 1987.
Holzman et al., "A Novel Immediate–Early Response Gene of Endothelium Is Induced by Cytokines and Encodes a Secreted Protein", *Mol. Cell. Biol.* 10:5830–5838, 1990.
Ashkenazi et al., "Protection against endotoxic shock by a tumor necrosis factor receptor immunoadhesin", *Proc. Natl. Acad. Sci. USA* 88:10535–10539, 1991.
Byrn et al., "Biological properties of a CD4 immunoadhesin", *Nature* 344:667–670, 1990.

*Primary Examiner*—Marianne P. Allen
*Assistant Examiner*—Lorraine M. Spector
*Attorney, Agent, or Firm*—Kathryn A. Anderson

[57] ABSTRACT elk ligand (elk-L) polypeptides as well as DNA sequences, vectors and transformed host cells useful in providing elk-L polypeptides. The elk-L polypeptide binds to a cell surface receptor that is a member of the tyrosine kinase receptor family.

10 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1041 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
        ( A ) NAME/KEY: CDS
        ( B ) LOCATION: 1..1041

( i x ) FEATURE:
        ( A ) NAME/KEY: mat_peptide
        ( B ) LOCATION: 73..1038

( x i ) SEQUENCE DESCRIPTION: SEQ ID NO:1:

```
ATG GCT CGG CCT GGG CAG CGT TGG CTC GGC AAG TGG CTT GTG GCG ATG     48
Met Ala Arg Pro Gly Gln Arg Trp Leu Gly Lys Trp Leu Val Ala Met
-24              -20                  -15                  -10

GTC GTG TGG GCG CTG TGC CGG CTC GCC ACA CCG CTG GCC AAG AAC CTG     96
Val Val Trp Ala Leu Cys Arg Leu Ala Thr Pro Leu Ala Lys Asn Leu
             -5                   1                   5

GAG CCC GTA TCC TGG AGC TCC CTC AAC CCC AAG TTC CTG AGT GGG AAG    144
Glu Pro Val Ser Trp Ser Ser Leu Asn Pro Lys Phe Leu Ser Gly Lys
        10                  15                  20

GGC TTG GTG ATC TAT CCG AAA ATT GGA GAC AAG CTG GAC ATC ATC TGC    192
Gly Leu Val Ile Tyr Pro Lys Ile Gly Asp Lys Leu Asp Ile Ile Cys
25                  30                  35                  40

CCC CGA GCA GAA GCA GGG CGG CCC TAT GAG TAC TAC AAG CTG TAC CTG    240
Pro Arg Ala Glu Ala Gly Arg Pro Tyr Glu Tyr Tyr Lys Leu Tyr Leu
                45                  50                  55

GTG CGG CCT GAG CAG GCA GCT GCC TGT AGC ACA GTT CTC GAC CCC AAC    288
Val Arg Pro Glu Gln Ala Ala Ala Cys Ser Thr Val Leu Asp Pro Asn
        60                  65                  70

GTG TTG GTC ACC TGC AAT AGG CCA GAG CAG GAA ATA CGC TTT ACC ATC    336
Val Leu Val Thr Cys Asn Arg Pro Glu Gln Glu Ile Arg Phe Thr Ile
        75                  80                  85

AAG TTC CAG GAG TTC AGC CCC AAC TAC ATG GGC CTG GAG TTC AAG AAG    384
Lys Phe Gln Glu Phe Ser Pro Asn Tyr Met Gly Leu Glu Phe Lys Lys
        90                  95                  100
```

| | | | | | | | | | | | | | | | | |
|---|---|---|---|---|---|---|---|---|---|---|---|---|---|---|---|---|
| CAC | CAT | GAT | TAC | TAC | ATT | ACC | TCA | ACA | TCC | AAT | GGA | AGC | CTG | GAG | GGG | 432 |
| His | His | Asp | Tyr | Tyr | Ile | Thr | Ser | Thr | Ser | Asn | Gly | Ser | Leu | Glu | Gly | |
| 105 | | | | 110 | | | | | 115 | | | | | | 120 | |
| CTG | GAA | AAC | CGG | GAG | GGC | GGT | GTG | TGC | CGC | ACA | CGC | ACC | ATG | AAG | ATC | 480 |
| Leu | Glu | Asn | Arg | Glu | Gly | Gly | Val | Cys | Arg | Thr | Arg | Thr | Met | Lys | Ile | |
| | | | | 125 | | | | | 130 | | | | | 135 | | |
| ATC | ATG | AAG | GTT | GGG | CAA | GAT | CCC | AAT | GCT | GTG | ACG | CCT | GAG | CAG | CTG | 528 |
| Ile | Met | Lys | Val | Gly | Gln | Asp | Pro | Asn | Ala | Val | Thr | Pro | Glu | Gln | Leu | |
| | | | 140 | | | | | 145 | | | | | 150 | | | |
| ACT | ACC | AGC | AGG | CCC | AGC | AAG | GAG | GCA | GAC | AAC | ACT | GTC | AAG | ATG | GCC | 576 |
| Thr | Thr | Ser | Arg | Pro | Ser | Lys | Glu | Ala | Asp | Asn | Thr | Val | Lys | Met | Ala | |
| | | 155 | | | | | 160 | | | | | 165 | | | | |
| ACA | CAG | GCC | CCT | GGT | AGT | CGG | GGC | TCC | CTG | GGT | GAC | TCT | GAT | GGC | AAG | 624 |
| Thr | Gln | Ala | Pro | Gly | Ser | Arg | Gly | Ser | Leu | Gly | Asp | Ser | Asp | Gly | Lys | |
| | 170 | | | | | 175 | | | | | 180 | | | | | |
| CAT | GAG | ACT | GTG | AAC | CAG | GAA | GAG | AAG | AGT | GGC | CCA | GGT | GCA | AGT | GGG | 672 |
| His | Glu | Thr | Val | Asn | Gln | Glu | Glu | Lys | Ser | Gly | Pro | Gly | Ala | Ser | Gly | |
| 185 | | | | | 190 | | | | | 195 | | | | | 200 | |
| GGC | AGC | AGC | GGG | GAC | CCT | GAT | GGC | TTC | TTC | AAC | TCC | AAG | GTG | GCA | TTG | 720 |
| Gly | Ser | Ser | Gly | Asp | Pro | Asp | Gly | Phe | Phe | Asn | Ser | Lys | Val | Ala | Leu | |
| | | | | 205 | | | | | 210 | | | | | 215 | | |
| TTC | GCG | GCT | GTC | GGT | GCC | GGT | TGC | GTC | ATC | TTC | CTG | CTC | ATC | ATC | ATC | 768 |
| Phe | Ala | Ala | Val | Gly | Ala | Gly | Cys | Val | Ile | Phe | Leu | Leu | Ile | Ile | Ile | |
| | | | 220 | | | | | 225 | | | | | 230 | | | |
| TTC | CTG | ACG | GTC | CTA | CTA | CTG | AAG | CTA | CGC | AAG | CGG | CAC | CGC | AAG | CAC | 816 |
| Phe | Leu | Thr | Val | Leu | Leu | Leu | Lys | Leu | Arg | Lys | Arg | His | Arg | Lys | His | |
| | | 235 | | | | | 240 | | | | | 245 | | | | |
| ACA | CAG | CAG | CGG | GCG | GCT | GCC | CTC | TCG | CTC | AGT | ACC | CTG | GCC | AGT | CCC | 864 |
| Thr | Gln | Gln | Arg | Ala | Ala | Ala | Leu | Ser | Leu | Ser | Thr | Leu | Ala | Ser | Pro | |
| | 250 | | | | | 255 | | | | | 260 | | | | | |
| AAG | GGG | GGC | AGT | GGC | ACA | GCG | GGC | ACC | GAG | CCC | AGC | GAC | ATC | ATC | ATT | 912 |
| Lys | Gly | Gly | Ser | Gly | Thr | Ala | Gly | Thr | Glu | Pro | Ser | Asp | Ile | Ile | Ile | |
| 265 | | | | | 270 | | | | | 275 | | | | | 280 | |
| CCC | TTA | CGG | ACT | ACA | GAG | AAC | AAC | TAC | TGC | CCC | CAC | TAT | GAG | AAG | GTG | 960 |
| Pro | Leu | Arg | Thr | Thr | Glu | Asn | Asn | Tyr | Cys | Pro | His | Tyr | Glu | Lys | Val | |
| | | | | 285 | | | | | 290 | | | | | 295 | | |
| AGT | GGG | GAC | TAC | GGG | CAC | CCT | GTC | TAC | ATC | GTC | CAA | GAG | ATG | CCG | CCC | 1008 |
| Ser | Gly | Asp | Tyr | Gly | His | Pro | Val | Tyr | Ile | Val | Gln | Glu | Met | Pro | Pro | |
| | | | 300 | | | | 305 | | | | | 310 | | | | |
| CAG | AGC | CCG | GCG | AAC | ATC | TAC | TAC | AAG | GTC | TGA | | | | | | 1041 |
| Gln | Ser | Pro | Ala | Asn | Ile | Tyr | Tyr | Lys | Val | | | | | | | |
| | 315 | | | | | 320 | | | | | | | | | | |

( 2 ) INFORMATION FOR SEQ ID NO:2:

( i ) SEQUENCE CHARACTERISTICS:
        ( A ) LENGTH: 346 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Arg | Pro | Gly | Gln | Arg | Trp | Leu | Gly | Lys | Trp | Leu | Val | Ala | Met |
| -24 | | | | -20 | | | | -15 | | | | -10 | | | |
| Val | Val | Trp | Ala | Leu | Cys | Arg | Leu | Ala | Thr | Pro | Leu | Ala | Lys | Asn | Leu |
| | | | -5 | | | | | 1 | | | | 5 | | | |
| Glu | Pro | Val | Ser | Trp | Ser | Ser | Leu | Asn | Pro | Lys | Phe | Leu | Ser | Gly | Lys |
| | | 10 | | | | 15 | | | | 20 | | | | | |
| Gly | Leu | Val | Ile | Tyr | Pro | Lys | Ile | Gly | Asp | Lys | Leu | Asp | Ile | Ile | Cys |
| 25 | | | | 30 | | | | 35 | | | | | | 40 | |

-continued

```
Pro   Arg   Ala   Glu   Ala   Gly   Arg   Pro   Tyr   Glu   Tyr   Tyr   Lys   Leu   Tyr   Leu
                         45                      50                            55

Val   Arg   Pro   Glu   Gln   Ala   Ala   Ala   Cys   Ser   Thr   Val   Leu   Asp   Pro   Asn
                  60                      65                                  70

Val   Leu   Val   Thr   Cys   Asn   Arg   Pro   Glu   Gln   Glu   Ile   Arg   Phe   Thr   Ile
            75                            80                            85

Lys   Phe   Gln   Glu   Phe   Ser   Pro   Asn   Tyr   Met   Gly   Leu   Glu   Phe   Lys   Lys
      90                            95                        100

His   His   Asp   Tyr   Tyr   Ile   Thr   Ser   Thr   Ser   Asn   Gly   Ser   Leu   Glu   Gly
105                           110                         115                             120

Leu   Glu   Asn   Arg   Glu   Gly   Gly   Val   Cys   Arg   Thr   Arg   Thr   Met   Lys   Ile
                        125                         130                              135

Ile   Met   Lys   Val   Gly   Gln   Asp   Pro   Asn   Ala   Val   Thr   Pro   Glu   Gln   Leu
                  140                         145                         150

Thr   Thr   Ser   Arg   Pro   Ser   Lys   Glu   Ala   Asp   Asn   Thr   Val   Lys   Met   Ala
            155                         160                         165

Thr   Gln   Ala   Pro   Gly   Ser   Arg   Gly   Ser   Leu   Gly   Asp   Ser   Asp   Gly   Lys
      170                         175                         180

His   Glu   Thr   Val   Asn   Gln   Glu   Glu   Lys   Ser   Gly   Pro   Gly   Ala   Ser   Gly
185                           190                         195                             200

Gly   Ser   Ser   Gly   Asp   Pro   Asp   Gly   Phe   Phe   Asn   Ser   Lys   Val   Ala   Leu
                        205                         210                              215

Phe   Ala   Ala   Val   Gly   Ala   Gly   Cys   Val   Ile   Phe   Leu   Leu   Ile   Ile   Ile
                  220                         225                         230

Phe   Leu   Thr   Val   Leu   Leu   Leu   Lys   Leu   Arg   Lys   Arg   His   Arg   Lys   His
            235                         240                         245

Thr   Gln   Gln   Arg   Ala   Ala   Ala   Leu   Ser   Leu   Ser   Thr   Leu   Ala   Ser   Pro
      250                         255                         260

Lys   Gly   Gly   Ser   Gly   Thr   Ala   Gly   Thr   Glu   Pro   Ser   Asp   Ile   Ile   Ile
265                           270                         275                             280

Pro   Leu   Arg   Thr   Thr   Glu   Asn   Asn   Tyr   Cys   Pro   His   Tyr   Glu   Lys   Val
                  285                         290                         295

Ser   Gly   Asp   Tyr   Gly   His   Pro   Val   Tyr   Ile   Val   Gln   Glu   Met   Pro   Pro
                  300                         305                         310

Gln   Ser   Pro   Ala   Asn   Ile   Tyr   Tyr   Lys   Val
            315                         320
```

CYTOKINE DESIGNATED ELK LIGAND

CROSS-REFERENCE TO RELATED APPLICATIONS

This application is a divisional of application Ser. No. 08/213,403, filed Mar. 15, 1994, issued Apr. 30, 1996 as U.S. Pat. No. 5,512,457 which is a continuation-in-part of application Ser. No. 07/977,693, filed Nov. 13, 1992, now abandoned.

BACKGROUND OF THE INVENTION

The cell surface protein designated elk is a member of a family of proteins known as the tyrosine kinase receptors. Proteins of this family have an intrinsic kinase activity that is activated upon ligand binding. A partial clone of elk was first discovered in a rat brain cDNA expression library that was screened for proteins expressing tyrosine kinase activity (Letwin et al., *Oncogene* 3:621, 1988). Later, a composite sequence spanning the entire ell coding region was derived from partial clones isolated from a rat brain cDNA library and a rat cerebellar brain library using the partial clone as a probe (Lhotak et al., *Mol. Cell. Biol.* 11:2496, 1991). The elk protein is very closely related to a number of other receptor tyrosine kinases, including hek (Boyd et al. *J. Biol. Chem.* 267:3262, 1992 and Wicks et al. *Proc. Natl. Acad. Sci. USA* 89:1611, 1992); the hek homologs mek4 and cek4 (Sajjadi et al. *New Biol.* 3:769, 1991); eek (Chan et al. *Oncogene* 6:1057, 1991); erk (Chan et al. supra), eck (Lindberg et al. *Mol. Cell. Biol.* 10:6316, 1990); cek5 (Pasquale, E. B. *Cell Regulation* 2:523, 1991); and eph (Hirai et al. *Science* 238:1717, 1987). The proteins of this subfamily are related not only in their cytoplasmic domains, but also in their extracellular domains, which are 41 to 68% identical. Interestingly, the tissue distributions of these various receptors are diverse. For example, expression of elk mRNA has been shown to be limited to testis and brain (Lhotak et al., supra), whereas eck is found not only in these same two tissues but in lung, intestine, kidney, spleen, ovary, and skin as well.

Ligands for the receptor tyrosine kinases are a diverse group of proteins that affect the growth, differentiation, and survival of cells expressing the receptors. To date, no ligand for elk has been discovered. Identification of the putative ligand would prove useful in investigating the nature of cellular processes that might be regulated by the elk protein.

SUMMARY OF THE INVENTION

The present invention provides a novel cytokine designated elk ligand (elk-L) that binds to the rat cell surface receptor known as elk. The present invention also provides isolated DNA encoding the elk-L protein, expression vectors comprising the isolated DNA, and a method for producing elk-L by cultivating host cells containing the expression vectors under conditions appropriate for expression of the elk-L protein. Antibodies directed against the elk-L protein or an immunogenic fragment thereof are also disclosed.

DETAILED DESCRIPTION OF THE INVENTION.

A cDNA encoding a novel protein ligand that binds to the rat cell surface protein known as elk has been isolated in accordance with the present invention. Also provided are expression vectors comprising the elk ligand (elk-L) cDNA and methods for producing recombinant elk-L polypeptides by cultivating host cells containing the expression vectors under conditions appropriate for expression of elk-L, and recovering the expressed elk-L. Purified elk-L protein is also encompassed by the present invention, including soluble forms of the protein comprising the extracellular domain.

The present invention also provides elk-L or antigenic fragments thereof that can act as immunogens to generate antibodies specific to the elk-L immunogens. Monoclonal antibodies specific for elk-L or antigenic fragments thereof thus can be prepared.

The novel cytokine disclosed herein is a ligand for elk, a rat cell surface receptor that is a member of the tyrosine kinase receptor family. Binding of elk-L to elk on the cell surface is believed to initiate a biological signal mediated by elk. One use of the elk ligand of the present invention is as a research tool for studying the nature of this biological signal and the role that elk-L, in conjunction with elk, may play in growth or differentiation of cells bearing the elk receptor. Expression of elk mRNA has been detected in the brain and testis of rats (Lhotok et al., supra), and the possibility that elk is capable of oncogenic activation has been suggested (Letwin et al., supra). The elk-L polypeptides of the present invention also may be employed in in vitro assays for detection of elk or elk-L or the interactions thereof. The human elk-L disclosed herein also finds use in identifying the putative human homolog of rat elk.

The elk-L protein exhibits neuroprotective and neurotrophic properties, as described in example 10. In one embodiment of the invention, elk-L inhibits neuronal death caused at least in part by the mechanism known as excitotoxicity. The use of elk-L in treating neurodegenerative diseases or injury to neurons is described in more detail below.

To identify cells suitable for use as nucleic acid sources in the cloning attempt, over 30 different types of murine and human cells were screened for the ability to bind elk (in the form of a fusion protein comprising rat elk and an antibody Fc polypeptide). As described in example 2, none of the cell types exhibited detectable elk binding. Since placental tissue is rich in growth and differentiation factors, a human placental cDNA expression library was screened with rat elk/Fc in art attempt to isolate an elk-L clone. Although it was not known whether or not placenta expressed an elk-L, and the ability of rat elk to bind to human elk-L also was unknown, human elk-L cDNA was successfully isolated as described in example 3. The DNA sequence and encoded amino acid sequence of the coding region of a human elk-L cDNA clone are set forth in SEQ ID NO: 1 and SEQ ID NO:2.

Human elk-L cDNA comprising the coding region was isolated from the positive clone and inserted into the Sma I site (in the multiple cloning site region of cloning vector pBLUESCRIPT® SK(−), available from Stratagene Cloning Systems, La Jolla, Calif. The resulting recombinant vector, designated tele 7 in pBLUESCRIPT® SK(−), in *E. coli* DH5α cells, was deposited with the American Type Culture Collection on Oct. 9, 1992, and assigned accession no. ATCC 69085. The deposit was made under the terms of the Budapest Treaty.

Comparison of both the nucleotide and encoded amino acid sequences of the human elk-L cDNA clone with the Genbank and Swisspro databases showed that the sequence of the elk ligand was unique. One amino acid sequence was identified in this search that did share limited sequence identity with the elk ligand. That sequence was for the B61 protein, which has previously been identified as the product of a novel immediate-early response gene induced by TNF in human umbilical vein endothelial cells (Holzman et al.,

*Mol. Cell. Biol.* 10:5830, 1990). All four of the cysteine residues in the extracellular domain of the two proteins are conserved, and the overall amino acid identity between human elk-L and B61 is 33%. In contrast to the elk ligand, the B61 protein has been reported to be secreted, but terminates with a hydrophobic tail and has been suggested to be associated with the membrane through a glycosylphosphatidyl inositol linkage (Holzman et al., supra ). The function of the B61 protein is unknown.

The term "elk-L" as used herein refers to a genus of polypeptides which are capable of binding elk. Human elk-L is within the scope of the present invention, as are elk-L proteins derived from other mammalian species including but not limited to murine, rat, bovine, porcine, or various primate cells. As used herein, the term "elk-L" includes membrane-bound proteins (comprising a cytoplasmic domain, a transmembrane region, and an extracellular domain) as well as truncated proteins that retain the elk-binding property. Such truncated proteins include, for example, soluble elk-L comprising only the extracellular (receptor binding) domain.

The human elk-L cDNA may be radiolabeled and used as a probe to isolate other mammalian elk-L cDNAs by cross-species hybridization. For example, a cDNA library prepared from placental tissue of other mammalian species may be screened with radiolabeled human elk-L cDNA to isolate a positive clone. Alternatively, mRNAs isolated from various cell lines can be screened by Northern hybridization to determine a suitable source of mammalian elk-L mRNA for use in cloning an elk-L gene.

Although an elk/Fc fusion protein was employed in the screening procedure described in Example 3 below, elk can be used to screen clones and candidate cell lines for expression of elk-L proteins. The elk/Fc fusion protein, however, offers the advantage of being easily purified. In addition, disulfide bonds form between the Fc regions of two separate fusion protein chains, creating dimers. The dimeric elk/Fc receptor was chosen for the potential advantage of higher affinity binding of the elk ligand, in view of the possibility that the ligand being sought would be multimeric.

Other antibody Fc regions may be substituted for the human IgG1 Fc region described in Example 1. Other suitable Fc regions are those that can bind with high affinity to protein A or protein G, and include the Fc region of murine IgG1 or fragments of the human IgG1 Fc region, e.g., fragments comprising at least the hinge region so that interchain disulfide bonds will form.

One embodiment of the present invention provides soluble elk-L polypeptides. Soluble elk-L polypeptides comprise all or part of the extracellular domain of a native elk-L but lack the transmembrane region that would cause retention of the polypeptide on a cell membrane. Soluble elk-L polypeptides advantageously comprise the native (or a heterologous) signal peptide when initially synthesized to promote secretion, but the signal peptide is cleaved upon secretion of elk-L from the cell. The soluble elk-L polypeptides that may be employed retain the ability to bind the elk receptor. Soluble elk-L may also include part of the transmembrane region or part of the cytoplasmic domain or other sequences, provided that the soluble elk-L protein is capable of being secreted.

Soluble elk-L may be identified (and distinguished from its non-soluble membrane-bound counterparts) by separating intact cells which express the desired protein from the culture medium, e.g., by centrifugation, and assaying the medium (supernatant) for the presence of the desired protein. The presence of elk-L in the medium indicates that the protein was secreted from the cells and thus is a soluble form of the desired protein. Soluble elk-L may be a naturally-occurring form of this protein.

The use of soluble forms of elk-L is advantageous for certain applications. Purification of the proteins from recombinant host cells is facilitated, since the soluble proteins are secreted from the cells. Further, soluble proteins are generally more suitable for intravenous administration.

Examples of soluble elk-L polypeptides include those comprising the entire extracellular domain of a native elk-L protein. One such soluble elk-L protein comprises amino acids 1 (Ala) through 213 (Lys) of SEQ ID NO:2. When initially expressed within a host cell, the soluble protein may additionally compose one of the heterologous signal peptides described below that is functional within the host cells employed. Alternatively, the protein may comprise the native signal peptide, such that the elk-L comprises amino acids –24 (Met) through 213 (Lys) of SEQ ID NO:2. In one embodiment of the invention, soluble elk-L is initially expressed as a fusion protein comprising (from N- to C-terminus) the yeast α factor signal peptide, the FLAG®peptide described below and in U.S. Pat. No. 5,011,912, and soluble elk-L comprising amino acids 1–213 of SEQ ID NO:2. This recombinant fusion protein is expressed in and secreted from yeast cells. The FLAG® peptide facilitates purification of the protein, and subsequently may be cleaved from the soluble elk-L using bovine mucosal enterokinase. DNA sequences encoding soluble elk-L proteins are encompassed by the present invention.

Truncated elk-L, including soluble polypeptides, may be prepared by any of a number of conventional techniques. A desired DNA sequence may be chemically synthesized using known techniques. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA :fragment into an expression vector, or the fragment may be digested at cleavage sites naturally present therein. The well known polymerase chain reaction procedure also may be employed to isolate a DNA sequence encoding a desired protein fragment. As a further alternative, known mutagenesis techniques may be employed to insert a stop codon at a desired point, e.g., immediately downstream of the codon for the last amino acid of the extracellular domain.

In another approach, enzymatic treatment (e.g., using Bal 31 exonuclease) may be employed to delete terminal nucleotides from a DNA fragment to obtain a fragment having a particular desired terminus. Among the commercially available linkers are those that can be ligated to the blunt ends produced by Bal 31 digestion, and which contain restriction endonuclease cleavage site(s). Alternatively, oligonucleotides that reconstruct the N- or C-terminus of a DNA fragment to a desired point may be synthesized. The oligonucleotide may contain a restriction endonuclease cleavage site, upstream of the desired coding sequence and position an initiation codon (ATG) at the N-terminus of the coding sequence.

The present invention provides purified elk-L polypeptides, both recombinant and non-recombinant. Variants and derivatives of native elk-L proteins that retain the desired biological activity (e.g., the ability to bind elk) are also within the scope of the present invention. elk-L variants may be obtained by mutations of nucleotide sequences coding for native elk-L polypeptides. An elk-L variant, as referred to herein, is a polypeptide substantially homologous to a native elk-L, but which has an amino acid sequence different from that of native elk-L (human, murine or other mammalian species) because of one or more deletions, insertions or substitutions.

The variant amino acid sequence preferably is at least 80% identical to a native elk-L amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981 ); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, which are incorporated by reference herein.

Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

elk-L also may be modified to create elk-L derivatives by forming covalent or aggregative conjugates with other chemical moieties, such as glycosyl groups, lipids, phosphate, acetyl groups and the like. Covalent derivatives of elk-L may be prepared by linking the chemical moieties to functional groups oft elk-L amino acid side chains or at the N-terminus or C-terminus of a elk-L polypeptide or the extracellular domain thereof. Other derivatives of elk-L within the scope of this invention include covalent or aggregative conjugates of elk-L or its fragments with other proteins or polypeptides, such as by synthesis in recombinant culture as N-terminal or C-terminal fusions. For example, the conjugate may comprise a signal or leader polypeptide sequence (e.g. the α-factor leader of Saccharomyces) at the N-terminus of a elk-L polypeptide. The signal or leader peptide co-translationally or post-translationally directs transfer of the conjugate from its site of synthesis to a site inside or outside of the cell membrane or cell wall.

elk-L polypeptide fusions can comprise peptides added to facilitate purification and identification of elk-L. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (DYKDDDDK), which is highly antigenic and provides an epitope reversibly bound by a specific monoclonal antibody enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*. A murine hybridoma designated 4E11 produces a monoclonal antibody that binds the peptide DYKDDDDK in the presence of certain divalent metal cations (as described in U.S. Pat. 5,011,912, hereby incorporated by reference) and has been deposited with the American Type Culture Collection under accession no HB 9259.

The present invention further includes elk-L polypeptides with or without associated native-pattern glycosylation. elk-L expressed in yeast or mammalian expression systems (e.g., COS-7 cells) may be similar to or significantly different from a native elk-L polypeptide in molecular weight and glycosylation pattern, depending upon the choice of expression system. Expression of elk-L polypeptides in bacterial expression systems, such as *E. coli*, provides non-glycosylated molecules.

DNA constructs that encode various additions or substitutions of amino acid residues or sequences, or deletions of terminal or internal residues or sequences not needed for biological activity or binding can be prepared. For example, N-glycosylation sites in the elk-L extracellular domain can be modified to preclude glycosylation, allowing expression of a more homogeneous, reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The human elk-L protein comprises one such triplet, at amino acids 115–117 of SEQ ID NO:2. Appropriate modifications to the nucleotide sequence encoding this triplet will result in substitutions, additions or deletions that prevent attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other variants are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. Human elk-L contains three KEX2 protease processing sites at amino acids 242–243, 243–244, and 246–247 of SEQ ID NO:2.

Naturally occurring elk-L variants are also encompassed by the present invention. Examples of such variants are proteins that result from alternative mRNA splicing events or from proteolytic cleavage of the elk-L protein, where, in the elk-binding property is retained. Alternative splicing of mRNA may yield a truncated but biologically active elk-L protein, such as a naturally occurring soluble form of the protein, for example. Variations attributable to proteolysis include, for example, differences in the N- or C-termini upon expression in different types of host cells, due to proteolytic removal of one or more terminal amino acids from the elk-L protein (generally from 1–5 terminal amino acids).

Nucleic acid sequences within the scope of the present invention include isolated DNA and RNA sequences that hybridize to the native elk-L nucleotide sequences disclosed herein under conditions of moderate or severe stringency, and which encode biologically active elk-L. Moderate stringency hybridization conditions refer to conditions described in, for example, Sambrook et al. *Molecular Cloning: A Laboratory Manual,* 2 ed. Vol. 1, pp. 1.101–104, Cold Spring Harbor Laboratory Press, (1989). Conditions of moderate stringency, as defined by Sambrook et al., include use of a prewashing solution of 5 X SSC, 0.5% SDS, 1.0 mM EDTA (pH 8.0) and hybridization conditions of about 55° C., 5 X SSC, overnight. Conditions of severe stringency include higher temperatures of hybridization and washing. The skilled artisan will recognize that the temperature and wash solution salt concentration may be adjusted as necessary according to factors such as the length of the probe.

Due to the known degeneracy of the genetic code wherein more than one codon can encode the same amino acid, a DNA sequence may vary from that presented in SEQ ID NO:1, and still encode an elk-L protein having the amino acid sequence of SEQ ID NO:1. Such variant DNA sequences may result from silent mutations (e.g., occurring during PCR amplification), and may be the product of deliberate mutagenesis of a native sequence.

The present invention thus provides isolated DNA sequences encoding biologically active elk-L, selected from: (a) DNA derived from the coding region of a native mammalian elk-L gene (e.g., cDNA comprising the nucleotide sequence presented in SEQ ID NO:1 ); (b) DNA capable of hybridization to a DNA of (a) under moderately stringent conditions and which encodes biologically active elk-L; and (c) DNA which is degenerate as a result of the genetic code to a DNA defined in (a) or (b) and which encodes biologically active elk-L. The elk-L proteins encoded by such DNA sequences are encompassed by the present invention.

Examples of elk-L proteins encoded by DNA that varies from the native DNA sequence of SEQ ID NO:1, wherein the variant DNA will hybridize to the native DNA sequence under moderately stringent conditions, include, but are not limited to, elk-L fragments (soluble or membrane-bound) and elk-L proteins comprising inactivated N-glycosylation site(s), inactivated KEX2 protease processing site(s), or conservative amino acid substitution(s), as described above. Elk-L proteins encoded by DNA drived from other mammalian species, wherein the DNA will hybridize to the human DNA of SEQ ID NO:1, are also encompassed.

Variants possessing the requisite ability to bind elk may be identified by any suitable assay. Biological activity of elk-L may be determined, for example, by competition for binding to the ligand binding domain of elk (i.e. competitive binding assays).

One type of a competitive binding assay for elk-L polypeptide uses a radiolabeled, soluble human elk-L and intact cells expressing cell surface elk. Instead of intact cells, one could substitute soluble elk (such as an elk/Fc fusion protein) bound to a solid phase through a Protein A or Protein G interaction with the Fc region of the fusion protein. Another type of competitive binding assay utilizes radiolabeled soluble elk such as an elk/Fc fusion protein, and intact cells expressing elk-L. Alternatively, soluble elk-L could be bound to a solid phase.

Competitive binding assays can be performed using standard methodology. For example, radiolabeled elk-L can be used to compete with a putative elk-L homolog to assay for binding activity against surface-bound elk. Qualitative results can be obtained by competitive autoradiographic plate binding assays, or Scatchard plots may be utilized to generate quantitative results.

Alternatively, soluble elk can be bound to a :solid phase such as a column chromatography matrix or a similar substrate suitable for analysis for the presence of a detectable moiety such as $^{125}$I. Binding to a solid phase can be accomplished, for example, by binding an elk/Fc fusion protein to a protein A or protein G-containing matrix.

The binding characteristics of elk-L (including variants) may also be determined using the conjugated, soluble elk (for example, $^{125}$I-elk/Fc) in competition assays similar to those described above. In this case, however, intact cells expressing elk-L, or soluble elk-L bound to a solid substrate, are used to measure the extent to which a sample containing a putative elk variant competes for binding of a conjugated soluble elk to elk-L.

The elk-L of the present invention can be used in a binding assay to detect cells expressing elk. For example, elk-L or an extracellular domain or a fragment thereof can be conjugated to a detectable moiety such as $^{125}$I. Radiolabeling with $^{125}$I can be performed by any of several standard methodologies that yield a functional $^{125}$I-elk-L molecule labeled to high specific activity. Alternatively, another detectable moiety such as an enzyme that can catalyze a colorometric or fluorometric reaction, biotin or avidin may be used. Cells to be tested for elk expression can be contacted with labeled elk-L. After incubation, unbound labeled elk-L is removed and binding is measured using the detectable moiety.

The elk ligand proteins disclosed herein also may be employed to measure the biological activity of elk protein in terms of binding affinity for elk-L. To illustrate, elk-L may be employed in a binding affinity study to measure the biological activity of an elk protein that has been stored at different temperatures, or produced in different cell types. The biological activity of an elk protein thus can be ascertained before it is used in a research study, for example.

Elk-L proteins find use as reagents that may be employed by those conducting "quality assurance" studies, e.g., to monitor shelf life and stability of elk protein under different conditions. Elk ligands may be used in determining whether biological activity is retained after modification of an elk protein (e.g., chemical modification, truncation, mutation, etc.). The binding affinity of the modified elk protein for an elk-L is compared to that of an unmodified elk protein to detect any adverse impact of the modifications on biological activity of elk.

A different use of an elk ligand is as a reagent in protein purification procedures. Elk-L or elk-L/Fc fusion proteins may be attached to a solid support material by conventional techniques and used to purify elk by affinity chromatography.

The elk-L protein exhibits neuroprotective properties. This property has been demonstrated in an assay in which neural death caused by treatment with glutamate (and believed to involve the mechanism known as excitotoxicity) was inhibited by elk-L. A trophic effect on neurons was also demonstrated, as described in example 10.

One embodiment of the present invention is thus directed to a method of treating disorders of neural tissue, such as injury and chronic or acute neurologic diseases, involving contacting the injured or diseased neurons with elk-L. Elk-L may be administered to a mammal to treat such an injury or disease. In one embodiment of the invention, elk-L is employed in treating an injury or disorder in which excitotoxicity plays a role, as discussed below.

Elk-L exhibits a trophic effect on neurons, whether or not the neurons are injured or afflicted with disease, and can be administered to a mammal to exert a trophic effect on neural tissue. In a patient suffering loss of or damage to neurons due to injury or disease, elk-L can be administered to enhance the viability of those neurons that have survived, regardless of the mechanism by which the loss or damage of neural tissue occurred. Examples of conditions that may be treated with elk-L include, but are not limited to, neuropathies such as diabetic, hereditary, and nutritional neuropathies, neurodegenerative diseases, and other disorders characterized by degeneration or loss of function of neurons.

Elk-L also finds use as a tissue culture reagent. An elk-L protein can be added to neurons cultured in vitro to enhance the viability and prolong the lifespan of the cultured neurons, thus facilitating research studies of neural tissue.

Certain acidic or sulfur-containing amino acids have been demonstrated to depolarize and excite neurons, such that prolonged exposure of neurons to high concentrations of such amino acids results in neural death (Olney et al. *Expl. Brain Res.* 14:61, 1971). This mechanism of neural death is known as excitotoxicity. A number of receptors for excitatory amino acids have been identified and characterized. In one embodiment of the invention, elk-L is administered to a mammal afflicted with a neurodegenerative condition characterized or mediated, at least in part, by excitotoxicity.

The major excitatory neurotransmitter in the central nervous system (CNS) is glutamate. Responsiveness to glutamate is a normal function in the developing and mature CNS. In addition to its normal role in excitatory synaptic transmission and plasticity, however, glutamate can also mediate or otherwise participate in a number of CNS dysfunctional states, including, but not limited to, measles, Alzheimer's disease, Huntington's Disease, Parkinsonism, stroke (ischemia), epilepsy, and AIDS-related dementia (reviewed in Meldrum and Garthwaite, *Trends Pharmacol. Sci.* 11:379, 1990; Choi, *J. Neurosci.* 10:2493, 1990; Lipton et al., *Neuron* 7:111, 1991; and Andersson et al., *Eur. J. Neurosci.* 3:66, 1991).

The involvement of an excitotoxic component in ischemic or hypoxic brain damage (e.g., resulting from a stroke) is well established (Choi, *Neuron* 1:623, 1988). Regarding AIDS related dementia, the HIV envelope glycoprotein gp 120 has been suggested to directly or indirectly enhance neuronal sensitivity to glutamate (Lipton, *Trends Neurol. Sci.* 15:75, 1992). Long term rat and primate models have been developed with excitotoxic insult that closely mimics the behavioral, neurochemical, and pathological defects associated with Huntington's disease (Beal, *Ann. Neurol.* 31:119, 1992). Deposition of amyloid plaques is a hallmark of Alzheimer's Disease (AD). Demonstration of an enhancing effect of β-amyloid on excitotoxicity in vitro (Koh et al., *Brain Res.* 533:315, 1990 and Mattson et al., *J. Neurosci.* 12:376, 1992) has led to the suggestion that β-amyloid potentiates slow excitotoxic neuronal death in vivo in AD patients. The accumulation of amyloid plaques in other conditions, including but not limited to Down's Syndrome and the aging process, likewise suggests a role for excitotoxicity.

Regarding Parkinson's Disease, the compound MPTP (1-methyl-4-phenyl-1,2,3,6-tetrahydropyridine) and its metabolite MPP$^+$ have been used to induce experimental parkinsonism. MPP$^+$kills dopaminergic neurons in the substantia nigra, yielding a reasonable model of late parkinsonism. Turski et al., (*Nature* 349:414, 1991) reported that antagonists of NMDA (an excitatory amino acid receptor) could protect the substantia nigra from MPP$^+$-mediated toxicity. This result has been confirmed and extended to demonstrate selective damage mediated by MPP$^+$, consistent with excitotoxicity (Storey et al., *J. Neurochem.* 58: 1975, 1992). A role for excitotoxicity in amyotrophic lateral sclerosis (ALS) has been proposed, based on extrapolation from data demonstrating a role for an excitatory amino acid in lathyrism (Spencer et al., *Lancet* 1:1066, 1986). The role of excitotoxicity in a number of neurological disorders, both acute and chronic, is further discussed in Albin, R. and J. Greenamyre, *Neurology* 42:733, 1992, and Beal, *Current Opinion in Neurobiol.* 2:657, 1992).

Several non-exclusive models for the precise: mechanism of excitotoxic damage to neurons have been proposed, including aberrant fluxes in intracellular $Ca^{++}$ leading to death, possibly through a nitric oxide intermediate. The production of free radicals is suggested to play a role in DNA damage leading to death (Garthwaite, *Trends Neurol. Sci.* 14:60, 1991 ). Another proposed mechanism involves defects in energy metabolism that cause neuronal death after excitotoxic injury (Lipton, *Trends Neurol. Sci.* 15:75, 1992). It is recognized that excitotoxic neuronal damage may occur via different mechanisms, depending on the nature of the condition involved. For example, defective receptors for excitatory amino acids may explain certain (e.g., inherited) disorders, whereas disorders characterized by late onset and slow progression may be attributable to impairment of cellular metabolism or membrane potential, wherein excitotoxicity is the final common pathway of neuronal death (Albin and Greenamyre, supra).

The present invention provides pharmaceutical compositions comprising an effective amount of a purified elk-L polypeptide and a suitable diluent, excipient, or carrier. Such carriers will be nontoxic to patients at the dosages and concentrations employed. Ordinarily, the preparation of such compositions entails combining a mammalian elk-L polypeptide or derivative thereof with buffers, antioxidants such as ascorbic acid, low molecular weight (less than about 10 residues) peptides, proteins, amino acids, carbohydrates including glucose, sucrose, or dextrans, chelating agents such as EDTA, glutathione, or other stabilizers and excipients. Neutral buffered saline is one appropriate diluent.

For therapeutic use, the compositions are administered in a manner and dosage appropriate to the indication and the patient. As will be understood by one skilled in the pertinent field, a therapeutically effective dosage will vary according to such factors as the nature and severity of the condition, the location of damaged neural tissue within the body in the case of an injury, and the age, condition and size of the patient. Administration may be by any suitable route, including but not limited to continuous infusion, local infusion during surgery, intraventricular infusion (which may involve use of an intraventricular catheter), sustained release from implants (gels, membranes, and the like), or injection (e.g., injection at the site of an injury or injection into the central nervous system).

The compositions of the present invention may contain an elk-L protein in any form described above, including variants, derivatives, and biologically active fragments thereof. In one embodiment of the invention the composition comprises a soluble human elk-L protein. Such protein may comprise the extracellular domain of human elk-L fused to an Fc polypeptide, as described above.

Elk-L derived from the same mammalian species as the patient is generally preferred for use in pharmaceutical compositions. However, elk-L appears to be highly conserved between species and has demonstrated cross-species reactivity for certain mammalian species.

Oligomeric Forms of Elk-L

Elk-L polypeptides may exist as oligomers, such as dimers or trimers. Oligomers are linked by disulfide bonds formed between cysteine residues on different elk-L polypeptides. In one embodiment of the invention, an elk-L dimer is created by fusing elk-L to the Fc region of an antibody (IgG 1) in a manner that does not interfere with binding of elk-L to the elk ligand binding domain. The Fc polypeptide preferably is fused to the C-terminus of a soluble elk-L (comprising only the extracellular domain). Preparation of fusion proteins comprising heterologous polypeptides fused to various portions of antibody-derived polypeptides (including the Fc domain) has been described, e.g., by Ashkenazi et al., (*PNAS USA* 88:10535, 1991) and Byrn et al., (*Nature* 344:677, 1990), hereby incorporated by reference. A gene fusion encoding the elk-L/Fc fusion protein is inserted into an appropriate expression vector. The elk-L/Fc fusion proteins are allowed to assemble much like antibody molecules, whereupon interchain disulfide bonds form between Fc polypeptides, yielding divalent elk-L. If fusion proteins are made with both heavy and light chains of an antibody, it is possible to form a elk-L oligomer with as many as four elk-L extracellular regions. Alternatively, one can link two soluble elk-L domains with a peptide linker such as the Gly$_4$SerGly$_5$Ser linker sequence described in U.S. Pat. No. 5,073,627.

The present invention provides oligomers of elk-L extracellular domains or fragments thereof, linked by disulfide interactions, or expressed, as fusion polymers with or without spacer amino acid linking groups. For example, a dimer of the elk-L extracellular domain can be linked by an IgG Fc region linking group.

Expression Systems

The present invention provides recombinant expression vectors for expression of elk-L, and host cells transformed with the expression vectors. Any suitable expression system may be employed. The vectors include an elk-L DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the elk-L DNA sequence. Thus, a promoter nucleotide sequence is operably linked to a elk-L DNA sequence if the promoter nucleotide sequence controls the transcription of the elk-L DNA sequence. The ability to replicate in the desired host cells, usually conferred by an origin of replication, and a selection gene by which transformants are identified, may additionally be incorporated into the expression vector.

In addition, sequences encoding appropriate signal peptides that are not native to the elk-L gene can be incorporated into expression vectors. For example, a DNA sequence for a signal peptide (secretory leader) may be fused in frame to the elk-L sequence so that the elk-L is initially translated as a fusion protein comprising the signal peptide. A signal peptide that is functional in the intended host cells enhances extracellular secretion of the elk-L polypeptide. The signal peptide is cleaved from the elk-L polypeptide upon secretion of elk-L from the cell.

Suitable host cells for expression of elk-L polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce elk-L polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, an elk-L polypeptide may include an N-terminal methionine residue to facilitate expression of the recombinant polypeptide in the prokaryotic host cell. The N-terminal Met may be cleaved from the expressed recombinant elk-L polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a elk-L DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ P$_L$ promoter and a cI857ts thermolabile repressor sequence. Plasmid vectors available from the American Type Culture Collection which incorporate derivatives of the λ P_L promoter include plasmid pHUB2 (resident in *E. coli* strain JMB9 (ATCC 37092)) and pPLc28 (resident in *E. coli* RR1 (ATCC 53082)).

elk-L alternatively may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2µ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the elk-L polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 µg/ml adenine and 20 µg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 µg/ml adenine and 80 µg/ml uracil. Derepression of the ADH2 promoter occurs when glucose is exhausted from the medium.

Mammalian or insect host cell culture systems could also be employed to express recombinant elk-L polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a vital genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. The vectors may be derived from retroviruses. In place of the native signal sequence, a heterologous signal sequence may be added, such as the signal sequence for interleukin-7 (IL-7) described in U.S. Pat. No. 4,965,195; the signal sequence for interleukin-2 receptor described in Cosman et al., *Nature* 312:768 (1984); the interleukin-4 signal peptide described in EP 367,566; the type I interleukin-1 receptor signal peptide described in U.S. Pat. No. 4,968,607; and the type II interleukin-1 receptor signal peptide described in EP 460,846.

Elk Ligand Protein

The present invention provides substantially homogeneous elk-L protein, which may be produced by recombinant expression systems as described above or purified from naturally occurring cells. The elk-L is purified to substantial homogeneity, as indicated by a single protein band upon analysis by SDS-polyacrylamide gel electrophoresis (SDS-PAGE).

One process for producing the elk-L protein comprises culturing a host cell transformed with an expression vector comprising a DNA sequence that encodes elk-L under conditions such that elk-L is expressed. The elk-L protein is then recovered from culture medium or cell extracts, depending upon the expression system employed. As the skilled artisan will recognize, procedures for purifying the recombinant elk-L will vary according to such factors as the type of host cells employed and whether or not the elk-L is secreted into the culture medium.

For example, when expression systems that secrete the recombinant protein are employed, the culture medium first may be concentrated using a commercially available protein concentration filter, for example, an Amicon or Millipore Pellicon ultra filtration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify elk-L. Some or all of the foregoing purification steps, in various combinations, can be employed to provide a substantially homogeneous recombinant protein.

It is also possible to utilize an affinity column comprising the ligand binding domain of elk to affinity-purify expressed elk-L polypeptides. elk-L polypeptides can be removed from an affinity column in a high salt elution buffer and then dialyzed into a lower salt buffer for use. Alternatively, the affinity column may comprise an antibody that binds elk-L. Example 4 describes a procedure for employing the elk-L protein of the present invention to generate monoclonal antibodies directed against elk-L.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express elk-L as a secreted polypeptide. This simplifies purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Nucleic Acid Fragments

The present invention further provides fragments of the elk-L nucleotide sequences presented herein. Such fragments desirably comprise at least about 14 nucleotides of the sequence presented in SEQ ID NO: 1. DNA and RNA complements of said fragments are provided herein, along with both single-stranded and double-stranded forms of the elk-L DNA.

Among the uses of such elk-L nucleic acid fragments is use as a probe. Such probes may be employed in cross-species hybridization procedures to isolate elk-L DNA from additional mammalian species. As one example, a probe corresponding to the extracellular domain of elk-L may be employed. The probes also find use in detecting the presence of elk-L nucleic acids in in vitro assays and in such procedures as Northern and Southern blots. Cell types expressing elk-L can be identified. Such procedures are well known, and the skilled artisan can choose a probe of suitable length, depending on the particular intended application.

Other useful fragments of the elk-L nucleic acids are antisense or sense oligonucleotides comprising a single-stranded nucleic acid sequence (either RNA or DNA) capable of binding to target elk-L mLRNA (sense) or elk-L DNA (antisense) sequences. Antisense or sense oligonucleotides, according to the present invention, comprise a fragment of the coding region of elk-L cDNA. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, Cancer Res. 48:2659, 1988 and van der Krol et al., *BioTechniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of elk-L proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence; specificity to be able to bind to target nucleotide sequences. Other examples of sense or antisense oligonucleotides include those oligonucleotides which are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oliginucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCTSA, DCTSB and DCTSC (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are provided to illustrate particular embodiments and not to limit the scope of the invention.

EXAMPLE 1

Preparation of Soluble elk/Fc Fusion protein

This example describes construction of an expression vector encoding a soluble elk/Fc fusion protein, for use in detecting cDNA clones encoding an elk ligand (elk-L). A DNA and encoded amino acid sequence for rat elk cDNA is presented in Lhotak et al. (*Mol. Cell. Biol.* 11:2496, 1991), hereby incorporated by reference. The rat elk protein has a 538 amino acid extracellular domain, a 25 amino acid transmembrane domain, and a 419 amino acid cytoplasmic domain.

A rat elk cDNA fragment was fused to the N-terminus of cDNA encoding the Fc portion of a human IgG 1 antibody. The rat elk cDNA was obtained from T. Pawson (Samuel Lunenfeld Research Institute, Mt. Sinai Hospital, Toronto). An Asp718 restriction endonuclease cleavage site was introduced upstream of the elk coding region. An Asp 718-BglII fragment of rat elk cDNA (comprising the entire extracellular domain, the transmembrane region, and a small portion of the cytoplasmic domain) was isolated.

DNA encoding a single chain polypeptide comprising the Fc region of a human IgG1 antibody was cloned into the SpeI site of the pBLUESCRIPT SK® vector, which is commercially available from Stratagene Cloning Systems, La Jolla, Calif. This plasmid vector is replicable in *E. coli* and contains a polylinker segment that includes 21 unique restriction sites. A unique BglII site was introduced near the 5' end of the inserted Fc encoding sequence, such that the BglII site encompasses the codons for amino acids three and four of the Fc polypeptide.

The encoded Fc polypeptide extends from the N-terminal hinge region to the native C-terminus, i.e., is an essentially full-length antibody Fc region. Fragments of Fc regions, e.g., those that are truncated at the C-terminal end, also may be employed. The fragments preferably contain multiple cysteine residues (at least the cysteine residues in the hinge reaction) to permit interchain disulfide bonds to form between the Fc polypeptide portions of two separate elk/Fc fusion proteins, forming dimers as discussed above.

The above-described Asp718-BglII elk cDNA fragment was cloned into the pBLUESCRIPT SK® vector containing the Fc cDNA, such that the elk cDNA is positioned upstream of the Fc cDNA. Single stranded DNA derived from the resulting gene fusion was mutagenized by the method described in Kunkel (*Proc. Natl. Acad. Sci. USA* 82:488, 1985) and Kunkel et al. (*Methods in Enzymol.* 154:367, 1987) in order to perfectly fuse the entire extracellular domain of elk to the Fc sequence. The mutagenized DNA was sequenced to confirm that the proper nucleotides had been removed (i.e., transmembrane region and partial cytoplasmic domain DNA was deleted) and that the elk and Fc sequences were in the same reading frame. The fusion cDNA was then excised and inserted into a mammalian expression vector designated pCAV/DHFR. The pCAV/DHFR vector is similar to pCAV/NOT, described in PCT Application WO 90/05183, but additionally contains a dihydrofolate reductase (DHFR) gene as a selectable marker. The DHFR gene confers a selective advantage on otherwise DHFR⁻ mammalian cells that have taken up the vector, when grown in the presence of methotrexate (MTX).

elk/Fc fusion proteins preferably are synthesized in recombinant mammalian cell culture. The elk/Fc fusion-containing expression vector was transfected into CV-1 cells (ATCC CCL 70) and COS-7 cells (ATCC CRL 1651), both derived from monkey kidney. The elk/Fc fusion protein expression level was relatively low in both CV-1 and COS-7 cells. Thus, expression in 293 cells (transformed primary human embryonal kidney cells, ATCC CRL 1573) was attempted.

The elk-Fc gene fusion was inserted into a mammalian expression vector designated HAV-EO (Dower et al., *J. Immunol.* 142:4314, 1989). 293 cells transfected with the HAV-EO/elk/Fc vector were cultivated in roller bottles to allow transient expression of the fusion protein, which is secreted into the culture medium via the elk signal peptide. The fusion protein was purified on protein A sepharose columns, eluted, and used to screen cells for the ability to bind the elk/Fc protein, as described in examples 2 and 3.

EXAMPLE 2

Screening Cells for elk/Fc Binding

Various cell types were screened for the ability to bind elk/Fc, to identify candidate cell types useful as nucleic acid sources in an attempt to clone an elk ligand. The recombinant rat elk/Fc protein produced and purified in example 1 was radiolabeled using a commercially available Enzymobead radioiodination reagent (BioRad) according to manufacturer's instructions. The $^{125}$I-elk/Fc protein did not show specific binding to any of several cell lines tested. Concern that direct labeling of the elk/Fc protein with Na$^{125}$I may have resulted in loss of biological activity led to the development of a two-step binding assay.

The two-step assay involved incubating cells with non-radiolabeled elk/Fc followed by $^{125}$I-mouse anti-human Fc antibody. The latter antibody will bind to the Fc portion of any elk/Fc fusion protein that has bound to the cells.

The mouse anti-human Fc antibody was obtained from Jackson Immunoresearch Laboratories, Inc., West Grove, Pa. This antibody showed minimal binding to Fc proteins bound to the Fcγ receptor. The antibody was labeled using the Chloramine T method. Briefly, a P6 column was prepared according to the manufacturer's instructions. In a microfuge tube, 10 μg of antibody was dissolved in 10 μl of PBS. 2000 μCi of carrier-free Na$^{125}$I was added and the solution was mixed well. 15 μl of a freshly prepared solution of chloramine-T (32 μg/ml in 0.05M sodium phosphate buffer (pH 7.2) was then added and the mixture was incubated for 30 minutes at room temperature. The mixture was immediately applied to the P6 column. The radiolabelled antibody was then eluted from the column by collecting 100–150 ul fractions of eluate. Binding media (RPMI 1640 containing 25 mg/ml bovine serum albumin, 2 mg/ml sodium azide, 20 mM Hepes pH 7.2) was added to peak fractions to bring the total volume of each fraction to 2 ml. Radioiodination yielded specific activities in the range of 5–10×10$^{15}$ cpm/mmol protein.

The screening procedure was as follows. Approximately 2×10$^6$ cells were cultured in 96-well plates. 150 μl binding medium was added to each well and the cells were then incubated in the presence or absence of elk/Fc for 1 hour at 37° C. with gentle agitation. The cells were sedimented from the mixture by centrifugation of the 96-well plates, washed with PBS, centrifuged again, and resuspended in binding medium. The cells were then incubated with the $^{125}$I-mouse anti-human Fc antibody, prepared as described above, for 1 hour at 37° C. Cells were also incubated with $^{125}$I-mouse anti-human Fc antibody in the presence of excess unlabelled anti-human Fc antibody as a negative control. Following a one hour incubation with the $^{125}$I-antibody, cells and unbound 125I-antibody were separated by the phthalate oil separation method, essentially as described by Dower et al., *J. Immunol.* 132:751, 1984. Cell-bound and free $^{125}$I-antibody were quantitated on a Packard Autogamma counter. No cell types were found to bind elk/Fc in this assay.

Cells, including additional cell types not previously screened, were assayed for elk/Fc binding by a third procedure. Cells were incubated with elk/Fc, followed by a biotinylated anti-human Fc antibody, followed by streptavidin-phycoerythrin (Becton Dickinson). The biotinylated antibody was purchased from Jackson Immunoresearch Laboratories. Streptavidin binds to the biotin molecule attached to the anti-human Fc antibody, which in turn binds to the Fc portion of the elk/Fc fusion protein. Phycoerythrin is a fluorescent phycobiliprotein which serves as a detectable label. The level of fluorescence signal was measured for each cell type using a FACScan® flow cytometer (Becton Dickinson).

The cells screened for the ability to bind elk/Fc by at least one of the three procedures described above included approximately 30 different cell types falling into the following general categories: primary murine fetal brain cells, murine fetal liver cell lines, murine fetal brain cell lines, and human lung carcinoma (fibroblastoid) cell lines. No cell types deemed positive for elk/Fc binding were identified.

EXAMPLE 3

Isolation of Elk Ligand cDNA from Human Placental cDNA Library

None of the cell types assayed in example 2 exhibited detectable elk/Fc binding. A human placental cDNA library was chosen as a possible source of elk ligand cDNA, since placental tissue is rich in growth and differentiation, factors. As discussed above, it is likely that the elk ligand plays a role in growth, survival, or differentiation of cells expressing elk (the corresponding receptor). However, the fact that placenta is relatively rich in Fc receptors posed a potential problem for the cloning attempt, since an elk/Fc fusion was used to screen clones.

A human placental cDNA library in plasmid pDC302 was prepared as described in Larsen et al. (*J. Exp. Med.,* 172:1559, 1990). pDC302 is a mammalian expression vector that also replicates in *E. coli* (Mosley et al., *Cell* 59:335, 1989). Briefly, placental cDNA was cloned into the BglII site of pDC302 by an adaptor method similar to that described by Haymerle et al (*Nucl. Acids Res.* 14:8615, 1986).

*E. coli* strain DH5α cells transfected with the placental cDNA library in pDC302 were plated to provide approximately 500 colonies per plate. Colonies were scraped from each plate, pooled, and plasmid DNA prepared from each pool. The pooled DNA representing about 2000 colonies was then used to transfect a sub-confluent layer of CV-1/EBNA-1 cells using DEAE-dextran followed by chloroquine treatment, similar to that described by Luthman et al., *Nucl. Acids Res.* 11:1295, 1983) and McCutchan et al., *J. Natl. Cancer Inst.* 41:351, 1986). The CV-1/EBNA-1 cell line (ATCC CRL10478) constitutively expresses EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

In order to transfect the CV-1/EBNA-1 cells with the cDNA library, the cells were maintained in complete medium (Dulbecco's modified Eagle's media (DMEM) containing 10% (v/v) fetal calf serum (FCS), 50 U/ml penicillin, 50 U/ml streptomycin, 2 mM L-glutamine) and were plated at a density of $2 \times 10^5$ cells/well on single-well chambered slides (Lab-Tek). Slides were pretreated with 1 ml human fibronectin (10 ug/ml in PBS) for 30 minutes followed by 1 wash with PBS. Media was removed from the adherent cell layer and replaced with 1.5 ml complete medium containing 66.6 µM chloroquine sulfate. 0.2 mls of DNA solution (2 µg DNA, 0.5 mg/ml DEAE-dextran in complete medium containing chloroquine) was then added to the cells and incubated for 5 hours. Following the incubation, the media was removed and the cells shocked by addition of complete medium containing 10% DMSO for 2.5 to 20 minutes followed by replacement of the solution with fresh complete medium. The cells were cultured for 2 to 3 days to permit transient expression of the inserted sequences.

Transfected monolayers of CV-1/EBNA-1 cells were assayed for expression of elk-L by slide autoradiography essentially as described by Gearing et al. (*EMBO J.* 8:3667, 1989). Transfected CV-1/EBNA-1 cells (adhered to chambered slides) were washed once with binding medium with nonfat dry milk (BM-NFDM) (RPMI medium 1640 containing 25 mg/ml bovine serum albumin (BSA), 2 mg/ml sodium azide, 20 mM HEPES, pH 7.2, and 50 mg/ml nonfat dry milk). Cells were then incubated with elk/Fc in BM-NFDM (1 µg/ml) for 1 hour at room temperature. After incubation, the cell monolayers in the chambered slides were washed three times with BM-NFDM to remove unbound elk/Fc fusion protein and then incubated with 40 ng/ml $^{125}$I-mouse anti-human Fc antibody prepared in example 2 (a 1:50 dilution) for 1 hour at room temperature. The cells were washed three times with BM-NFDM, followed by 2 washes with phosphate-buffered saline (PBS) to remove unbound 125I-mouse anti-human Fc antibody. The cells were fixed by incubating for 30 minutes at room temperature in 2.5% glutaraldehyde in PBS, pH 7.3, washed twice in PBS and air dried. The chamber slides containing the cells were exposed on a Phosphorimager (Molecular Dynamics) overnight, then dipped in Kodak GTNB-2 photographic emulsion (6× dilution in water) and exposed in the dark for 3–5 days at 4° C. in a light proof box. The slides were then developed for approximately 4 minutes in Kodak D19 developer (40 g/500 ml water), rinsed in water and fixed in Agfa G433C fixer. The slides were individually examined with a microscope at 25–40× magnification and positive cells expressing elk-L were identified by the presence of autoradiographic silver grains against a light background.

Using the slide autoradiography approach, approximately 300,000 cDNAs were screened in pools of approximately 2,000 cDNAs until assay of one transfectant pool showed multiple cells clearly positive for elk/Fc binding. This pool was then partitioned into pools of 500 and again screened by slide autoradiography and a positive pool was identified. Individual colonies from this pool of 500 were screened until a single clone (clone #E7) was identified which directed synthesis of a surface protein with detectable elk/Fc binding activity. This clone was isolated, and its cDNA insert was sequenced.

The nucleotide and encoded amino acid sequences of the coding region of the human elk ligand cDNA of clone E7 are presented in SEQ ID NOS:1 and 2. The cDNA insert is 2111 bp in length. There are three reasonably sized open reading frames within this sequence that could encode proteins of 82, 85, and 346 amino acids. Of these three, the two smallest open reading frames lack both good translation initiation codons as well as a signal sequence. Thus, DNA and encoded amino acid sequences for the 346-amino acid open reading frame are presented in SEQ ID NOS: 1 and 2. The protein of SEQ ID NO:2 is a type I transmembrane protein, with an N-terminal signal peptide (amino acids −24 to −1, an extracellular domain (amino acids 1–213) a transmembrane domain (amino acids 214–241) and a cytoplasmic domain (amino acids 242–322). The predicted molecular weight of the native protein following cleavage of the signal sequence is 35,180 daltons. The mature protein has an estimated pI of 9.006. There are 307 bp of 5' noncoding sequence and 763 bp of 3' non-coding sequence flanking the coding region.

Human elk-L cDNA was excised from clone E7 by digestion with Bsu36I (which cleaves downstream of the stop codon), followed by treatment with Klenow fragment to render the Bsu36I-digested end blunt, followed by digestion with SmaI (which cleaves upstream of the initiation codon and generates blunt: ends). The excised cDNA, which includes the entire coding region, was cloned into the SmaI site (in the multiple cloning site) of pBLUESCRIPT® SK(−) (Stratagene Cloning Systems, La Jolla, Calif.). The resulting vector (designated tele 7 in pBLUESCRIPT SK(−)) in *E. coli* DH5α cells was deposited with the American Type Culture Collection, Rockville, Md., USA (ATCC) on Oct. 9, 1992 and assigned accession number ATCC 69085. The deposit was made under the terms of the Budapest Treaty.

EXAMPLE 4

Monoclonal Antibodies to elk-L

This example illustrates the preparation of monoclonal antibodies to elk-L. elk-L is expressed in mammalian host cells such as COS-7 or CV-1/EBNA-1 cells and purified using elk/Fc affinity chromatography. Purified elk-L (or a fragment thereof such as the extracellular domain) can be used to generate monoclonal antibodies against elk-L using conventional techniques, for example, those techniques described in U.S. Pat. No. 4,411,993. Briefly, mice are immunized with elk-L as an immunogen emulsified in complete Freund's adjuvant, and injected in amounts ranging from 10–100 μg subcutaneously or intraperitoneally. Ten to twelve days later, the immunized animals are boosted with additional elk-L emulsified in incomplete Freund's adjuvant. Mice are periodically boosted thereafter on a weekly to bi-weekly immunization schedule. Serum samples are periodically taken by retro-orbital bleeding or tail-tip excision for testing by dot blot assay or ELISA (Enzyme-Linked Immunosorbent Assay), for elk-L antibodies.

Following detection of an appropriate antibody titer, positive animals are provided one last intravenous injection of elk-L in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified elk-L by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-elk-L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to elk-L.

EXAMPLE 5

Northern Blot Analyses

To investigate expression of elk-L in various tissues, a human tissue Northern blot that contained 2 ug of poly A$^+$ mRNA from a variety of tissues (available from Clonetech, Palo Alto, Calif.) was probed with an elk-L, riboprobe. 5' and 3' non-coding sequences were removed from the elk ligand cDNA by digesting with SmaI and BsuI and inserting the coding region into the pBluescript SK(−) vector (Stratagene Cloning Systems, LaJolla, Calif.). A riboprobe was prepared by cutting the elk-L cDNA with SilI and using the T3 RNA polymerase promoter to transcribe the 3' most 450 nucleotides of elk-L coding sequence. The blot was hybridized with the riboprobe at 63° C., then washed, first with 1XSSC/0.1% SDS for 1 h at 68° C., then with 0.1X SSC/0.1%SDS for 30 min at 68° C. The blot was exposed to X-ray film at −70° for 11 days sandwiched between two intensifying screens. A major 3.5 kb message was observed in heart, placenta, lung, liver, skeletal muscle, kidney, and pancreas.

The elk-L mRNA was not present in detectable levels in whole adult brain, even though brain and testis are the only tissues reported to express the elk receptor (Lhotak et al., supra). It is possible that expression in brain is at very low levels, or is limited to a distinct region(s), and therefore was not detected by the foregoing technique. To further investigate this issue, dissected brains from 8-day old and young adult rats were probed with an elk-L riboprobe. Elk-L appears to be expressed in the developing rat brain, with the highest level of expression in the olfactory bulb. Expression of elk-L in the olfactory bulb appears to continue into adulthood. Interestingly, the olfactory bulb is actively re-innervated throughout the life of the animal, in contrast to the rest of the brain.

A second Northern blot revealed that elk-L mRNA expression is upregulated by TNF in human umbilical vein endothelial cells (HUVECS). B61 mRNA in HUVECS was shown to be inducible by treating the cells with IL-1 or TNF (Holzman et al., supra). In view of the degree of homology between elk-L and B61, a Northern blot of HUVEC mRNA (from either resting cells or cells induced with TNF) was probed with the above-described elk-L riboprobe. The major 3.5 kb species seen in other tissues was specifically induced following treatment with TNF.

In a separate experiment, elk-L and elk mRNA were detected on cultured embryonic rat hippocampal and cortical neurons by Northern blot analysis.

EXAMPLE 6

Southern Blot Analysis

The presence of elk-L DNA in various species was investigated as follows. A blot consisting of EcoRI-digested DNAs from a variety of species (Clonetech, Palo Alto, Calif.) was prehybridized at 63° C. in prehybridization buffer. The blot was then probed with a random primed clone E7 probe (corresponding to the entire elk-L coding region) and washed to high stringency (1XSSC/0.1% SDS for 60 min at 63° C., then 0.1XSSC/0.1% SDS at 63° C. for 30 min). The image of the blot was developed on a Phosphorimager (Molecular Dynamics). The gene was found to be highly conserved in a wide variety of species, including monkey, rat, mouse, dog, cow, rabbit, chicken, and even yeast.

EXAMPLE 7

Binding Study

To examine the binding of elk-L to the elk receptor, a modified indirect Scatchard analysis was devised. This indirect assay was necessary because direct radiolabeling of elk/Fc inactivated the binding specificity of this protein. The assay procedure was as follows.

CV1-EBNA-1 cells (described in Example 3) in 12-well plates ($2.5\times10^5$ cells/well) were transfected with an expression vector containing the clone E7 elk-L cDNA. The mammalian expression vector, designated pDC410, is similar to pDC406 (McMahan et al., *EMBO J.* 10:2821, 1991). In pDC410, the EBV origin of replication of pDC406 is replaced by DNA encoding the SV40 large T antigen (driven from an SV40 promoter). The pDC410 multiple cloning site (mcs) differs from that of pDC406 in that it contains additional restriction sites and three stop codons (one in each reading frame). A T7 polymerase promoter downstream of the mcs facilitates sequencing of DNA inserted into the mcs. The transfected cells were cultured for two days to permit expression of the elk-L protein, then washed with BM-NFDM (the binding medium described in Example 2, also containing 50 mg/ml nonfat dry milk), and incubated with various concentrations of the elk/Fc fusion protein prepared in Example 1, for 1 hour at 37° C. Subsequently, cells were washed and incubated with a constant saturating concentration of the $^{125}$I-labeled mouse anti-human IgG antibody prepared in Example 2 (40 ng/ml) in binding medium with gentle agitation for 1 hour at 37° C. Cells then were harvested by trypsinization. In all assays, non-specific binding of $^{125}$I antibody was assayed in the absence of elk/Fc as well as in the presence of elk/Fc and a 200-fold molar excess of unlabeled mouse anti-human IgG antibody.

Free and cell-bound $^{125}$I-antibody were quantified on a Packard Autogamma Counter. The binding curve was replotted in the Scatchard coordinate system (Scatchard, Ann. N.Y. Acad. Sci. 51:660, 1949). Affinity calculations (Scatchard, Ann. N.Y. Acad. Sci. 51:660, 1949) were generated on RS/1 (BBN Software, Boston, Mass.) run on a Microvax computer. A single high affinity binding component was identified. The elk-L binding sites expressed on the CV-1 EBNA-1 transfectants had an affinity constant ($K_A$) of $1.08\times10^9$ M$^{-1}$ for elk/Fc. This affinity constant matches well with those observed for binding of elk/Fc to the native ligand expressed on various rat neural cell lines.

The ability of elk-L to bind to a receptor known as "hek" was investigated in the same assay. Hek, like elk, is a member of the eph/elk family of receptor tyrosine kinases. Boyd et al. (*J. Biol. Chem.* 267:3262, 1992) purified a cell surface glycoprotein exhibiting tyrosine kinase activity. The N-terminal amino acid sequence identified this protein as a member of the eph/elk family, and the protein was thus designated hek (human eph/elk-like kinase). Expression of hek transcripts on the human pre-B cell leukemia cell line LK63 and the human T-cell leukemia cell line JM, as well as on the human T-cell leukemia cell line HSB-2, has been demonstrated by northern blot analysis (Wicks et al., *Proc. Natl. Acad. Sci. USA* 89:1611, 1992). Nucleotide and amino acid sequences for an isolated hek cDNA clone are presented in Wicks et al., supra.

Two hek ligand proteins were included in the assay as well. The protein known as B61 (Holzman et al., *Mol. Cell. Biol.* 10:5830, 1990) was included in the study because of its degree of homology to elk-L (33% identity at the amino acid level).

Expression vector pDC4 10 containing DNA encoding B61 or a hek-L protein was substituted for the elk-L expression vector in the foregoing assay. Two hek-L proteins designated A2 and C6, which are 38% identical at the amino acid level, are described in co-pending U.S. application Ser. No. 08/161,132, hereby incorporated by reference. DNA and encoded amino acid sequences for the two hek-L proteins are presented in application Ser. No. 08/161,132. Nucleotide and encoded amino acid sequences for B61 cDNA are presented in Holzman et al., supra, hereby incorporated by reference.

A soluble hek/Fc fusion protein was prepared by procedures analogous to those described in example 1 for the soluble elk/Fc fusion protein. Production of hek/Fc is also described in application Ser. No. 08/161,132.

The results of the study were as follows:

TABLE I

| | Binding affinity for hek/Fc ($K_a$) |
|---|---|
| pDC410 | — |
| B61 | $5.5 \times 10^7$ M$^{-1}$ |
| elk-L | $2.3 \times 10^7$ M$^{-1}$; $2.9 \times 10^6$ M$^{-1}$ |
| hek-L A2 | $2.0 \times 10^8$ M$^{-1}$ |
| hek-L C6 | $2.0 \times 10^8$ M$^{-1}$ |

The empty vector exhibited no detectable hek/Fc binding. B61 bound hek/Fc with relatively moderate affinity, exhibiting a single affinity class of binding. The binding of hek/Fc to elk-L resulted in a biphasic pattern, indicating two lower-affinity binding components (affinity constants $2.3\times10^7$ M$^{-1}$ and $2.9\times10^6$ M$^{-1}$). The affinities of the two hek-L proteins for hek/Fc were equivalent and relatively high.

TABLE II

| | Binding affinity for elk/Fc ($K_a$) |
|---|---|
| B61 | $2.3 \times 10^8$ M$^{-1}$; $7.0 \times 10^7$ M$^{-1}$ |
| elk-L | $1.08 \times 10^9$ M$^{-1}$ |
| hek-L A2 | $2.7 \times 10^8$ M$^{-1}$; $3.5 \times 10^7$ M$^{-1}$ |
| hek-L C6 | $1.3 \times 10^8$ M$^{-1}$; $5.4 \times 10^7$ M$^{-1}$ |

A biphasic pattern of elk/Fc binding was observed for B61 with $K_a$s of $2.3\times10^8$ M$^{-1}$ and $7.0\times10^7$ M$^{-1}$. The affinity constant ($K_a$) shown for elk/Fc binding to transfected cells expressing elk-L matches well with those observed for binding of elk/Fc to the native ligand expressed on various rat neural cell lines. A biphasic pattern of elk/Fc binding is seen for both hek ligands.

EXAMPLE 8

Homology

The homology of the full length human elk-L, B61, hek ligand A2, and hek ligand C6 proteins (described in Example 5) for one another at the amino acid level are presented in Table III:

TABLE III

| | | % amino acid identity | | | |
|---|---|---|---|---|---|
| | | elk-L | B61 | A2 | C6 |
| % amino acid similarity | elk-L | | 33 | 28 | 32 |
| | B61 | 51 | | 40 | 37 |
| | A2 | 48 | 63 | | 38 |
| | C6 | 50 | 55 | 57 | |

The percent identity of the DNA sequences is presented in Table IV:

TABLE IV

| | % DNA identity | | | |
|---|---|---|---|---|
| | elk-L | B61 | A2 | C6 |
| elk-L | | 44.0 | 40.7 | 43.7 |
| B61 | | | 48.9 | 51.5 |
| A2 | | | | 47.3 |
| C6 | | | | |

EXAMPLE 9

Production of Soluble Elk-L/Fc Fusion Protein

A soluble fusion protein comprising the extracellular domain of human elk-L fused to the N-terminus of an Fc region polypeptide derived from a human IgG1 antibody was prepared as follows. Soluble elk-L is preferably expressed as an elk-L/Fc fusion protein. Among the advantages of expressing soluble elk-L as such a fusion protein is that the Fc moiety facillitates the protein purification process by binding to Protein A or Protein G on an affinity chromatography matrix.

The Fc polypeptide is an essentially full-length antibody Fc region, extending from the hinge region to the native C-terminus, as described in example 1. The nucleotide sequence of cDNA encoding the Fc polypeptide, along with the encoded amino acid sequence, are presented in PCT application publication no. WO 93/10151, hereby incorporated by reference.

DNA encoding the signal peptide and extracellular domain of human elk-L (amino acids −24 through 213 of SEQ ID NO:2) and DNA encoding the Fc polypeptide are inserted into a mammalian expression vector such that the Fc-encoding DNA is fused to the 3' end of the elk-L DNA. The vector, designated CAV, is essentially identical to vector pDC302 described in Mosley et al. *Cell* 59:335, 1989 (hereby incorporated by reference) except that CAV lacks a NotI site present in the multiple cloning site of pDC302. *E. coli* cells were transfected with the ligation mixture, and the desired recombinant vector was isolated from the transformants.

Chinese hamster ovary (CHO) cells were transfected with the recombinant vector. Other mammalian cell lines, such as CV 1 (ATCC C. CL 70) or 293 (ATCC CRL 1573) cells may be employed in place of the CHO cells. The transfected cells were cultured to produce the elk-L/Fc fusion protein, which was secreted into the culture medium. The elk-L/Fc proteins are believed to form dimers, wherein two such fusion proteins are joined by disulfide bonds that form between the Fc moieties thereof. The protein was recovered from the culture medium by a procedure that included affinity chromatography on a Protein A-bearing chromatography column.

EXAMPLE 10

Neuroprotective Effect of Elk-L

Elk-L demonstrated an ability to inhibit neuronal death in the following assay. A trophic effect of elk-L on neurons was also demonstrated. In the following assay, neural death results from a mechanism known as excitotoxicity, which is a mechanism implicated (at least to some degree) in a wide variety of neurodegenerative diseases.

Glass coverslips (12 mm, round) were first coated with poly-L-lysine (Sigma Chemical Co., St. Louis, Miss.), which is known to aid in vitro cultivation of neurons. Prior to cell plating, coverslips were incubated with a fusion protein comprising an Fc polypeptide (derived from a human IgG 1 antibody) fused to the C-terminus of the extracellular domain of one of the following proteins: elk, elk-L and B220 (also known as CD45, an irrelevant protein used as a negative control). Preparation of the soluble elk/Fc and elk-L/Fc fusion proteins is described in examples 1 and 9, respectively, and the B220/Fc fusion protein is prepared by analogous procedures. The incubation involved covering each coverslip with 150 µl of a solution containing 10 µg/ml of a fusion protein in PBS, and incubating at 37° C. for 1.5–hours. Coverslips then were washed three times in plating media. Control coverslips were coated with poly-L-lysine alone (no Fc fusion protein).

Hippocampal neurons were generated as described in Banker, G. and K. Goslin, *Culturing Nerve Cells*, Cambridge, MIT Press, 1992. Briefly, E18 pregnant Sprague-Dawley rats were euthanized with an overdose of metaphane. Hippocampi were dissected from fetuses, cut into approximately 1 mm pieces, and incubated for 13 minutes in HBBS (Hank's balanced salt solution with 10 mM HEPES) containing 0.2% trypsin. The tissue was then washed with neurobasal media with B27 supplement (GIBCO/BRL, Bethesda, Md.). Following enzymatic dissociation, the tissue was triturated with a fire-polished pipette in neurobasal media with B27. Cells were then plated onto the coverslips previously coated with substrates as described above. Cells were allowed to attach for 2–4 hours, then washed with fresh media to remove unattached cells. Cultures were grown at 37° C. in 5% $CO_2$ and the medium was changed about two times weekly.

After 9–10 days in culture, a stock solution of glutamate in culture medium was added to cultures to give a final concentration ranging from 1 mM to 1 µM. Negative control cultures were not treated with glutamate. Cells were viewed and photographed at 24 hour intervals for 4–6 days after addition of glutamate.

Results

Before glutamate treatment, neurons grew well on all substrates. Results at various timepoints after glutamate treatment were as follows.

24 hours post-treatment with 1 mM glutamate, neurons growing on poly-L-lysine were destroyed. Neurons growing on elk-L/Fc (understood to mean elk-L/Fc plus poly-L-lysine in the remainder of this example) were dying, but some neurons were still intact. In cultures treated with 100 µM glutamate, neurons growing on poly-L-lysine were beginning to deteriorate. In cultures growing on elk-L/Fc, neurons were dying and neurites were beady (swollen, with death imminent). In cultures treated with 10 µM glutamate, neurons on both substrates appeared healthy, however, in the poly-L-lysine cultures, there appeared to be a lot more debris.

48 hours post-treatment, all cultures exposed to 1 mM glutamate were dead. Poly-L-lysine cultures treated with 100 µM glutamate also were dead. Elk-L/Fc cultures treated with 100 µM glutamate were greatly deteriorated, but still contained some viable neurons. Neurons on poly-L-lysine, treated with 10 µM glutamate, were deteriorating (except cells in clumps) and no growth cones were seen. Neurons in cultures growing on elk-L/Fc, treated with 10µM glutamate, looked good. Although neurites were beady in areas of lower cell density, growth cones were visible. In cultures which did not receive treatment with glutamate, more neurons were viable and these neurons appeared healthier on elk-L than on poly-L-lysine.

3 days post-treatment, neurons in 1 mM or 100 µM glutamate were dead. However, the cultures grown on elk-L/Fc had a higher density and neurites were healthier than in the cultures grown on poly-L-lysine.

4 days post-treatment, cultures growing on poly-L-lysine in 10 µM glutamate showed substantial cell death and debris, and many neurites were destroyed. In cultures grown on elk-L/Fc in 10 µM glutamate, a higher cell density, less debris and healthier neurites were seen, except in areas of very low density.

5 days post treatment, cultures growing on poly-L-lysine with all concentrations of glutamate contained few surviving neurons and cultures without glutamate were deteriorated. Cultures growing on elk-L/Fc with glutamate 10 µM contained many cells, with healthy neurites in most areas (beady neurites being observed in only a few areas). Cultures not treated with glutamate grown on elk-L appear healthier and have a higher cell density (number of surviving cells) than cultures growing on poly-L-lysine alone.

In general, neurons growing on elk-L/Fc are healthier and survive for a longer period of time than neurons growing on poly-L-lysine. When challenged with glutamate, neurons growing on elk-L/Fc appear to be protected from excitotoxicity in comparison to neurons growing on poly-L-lysine.

Neither a protective nor a trophic effect was seen for cultures grown with B220/Fc and poly-L-lysine. Neurons growing on elk/Fc plus poly-L-lysine appeared to be sensitized to glutamate toxicity.

What is claimed is:

1. A substantially homogeneous purified mature elk-L protein, wherein said elk-L protein binds elk, wherein said elk-L protein comprises an amino acid sequence that is at least 80% identical to a sequence selected from the group consisting of amino acids 1–322 of SEQ ID NO:2 and amino acids 1–213 of SEQ ID NO:2.

2. Purified elk-L according to claim 1, wherein said elk-L comprises an amino acid sequence selected from the group consisting of amino acids 1–322 of SEQ ID NO:2 and 1–213 of SEQ ID NO:2.

3. A composition comprising an elk-L protein of claim 1 and a pharmaceutically acceptable diluent, excipient, or carrier.

4. A purified elk-L protein which binds elk, wherein said elk-L protein comprises modification(s) selected from the group consisting of:

(a) inactivation of N-glycosylation site(s); and (b) inactivation of KEX2 protease processing site(s); and wherein the amino acid sequence of said elk-L protein is otherwise identical to amino acids 1–322 or 1–213 of SEQ ID NO:2.

5. Essentially homogeneous purified elk-L protein, wherein said elk-L protein is a fragment of the amino acid sequence presented as amino acids 1–322 of SEQ ID NO:2, wherein said elk-L protein binds elk.

6. A purified elk-L protein which binds elk, wherein the mature form of said elk-L is characterized by:

a) a calculated molecular weight of about 35,180 daltons;

b) a pI of about 9.006; and c) the N-terminal amino acid sequence: Ala-Thr-Pro-Leu-Ala-Lys-Asn-Leu-Glu-Pro-Val-Ser-.

7. A purified elk-L protein that is a naturally occurring variant of the elk-L presented as amino acids 1–322 of SEQ ID NO:2, wherein:

a) the elk-L variant binds elk; b) the elk-L variant is encoded by a DNA which hybridizes under severely stringent conditions to a DNA consisting of nucleotides 1 to 1041 of SEQ ID NO:1; and c) the amino acid sequence of the elk-L variant is at least 80% identical to a sequence selected from the group consisting of amino acids 1–322 of SEQ ID NO:2 and amino acids 1–213 of SEQ ID NO:2.

8. A purified elk-L protein capable of binding elk, wherein said elk-L protein comprises an amino acid sequence that is at least 80% identical to a sequence selected from the group consisting of amino acids 1–322 of SEQ ID NO:2 and amino acids 1–213 of SEQ ID NO: 2.

9. A purified elk-L protein according to claim 8, wherein said elk-L protein comprises an amino acid sequence that is at least 90% identical to a sequence selected from the group consisting of amino acids 1–322 of SEQ ID NO:2 and amino acids 1–213 of SEQ ID NO: 2.

10. An elk-L protein encoded by the elk-L cDNA insert in the recombinant vector deposited in strain ATCC 69085.

* * * * *